United States Patent [19]

De Rocchis et al.

[11] Patent Number: 4,990,087

[45] Date of Patent: Feb. 5, 1991

[54] DENTAL TOOL MAINTENANCE APPARATUS AND METHOD

[76] Inventors: Louis G. De Rocchis, 608 Trout Lake Dr.; William M. Miller, 3741 McGrath Rd.; Bradley J. Robart, 2714 Lakeridge La., all of, Bellingham, Wash. 98226; David H. Bates, 1014 Talcott St., Sedro Woolley, Wash. 98284

[21] Appl. No.: 470,827

[22] Filed: Jan. 26, 1990

[51] Int. Cl.$^5$ ............................................. A61C 1/02
[52] U.S. Cl. ................................................... 433/104
[58] Field of Search .................. 433/104, 98; 184/6.3, 184/55.2

[56] References Cited

U.S. PATENT DOCUMENTS

| | | | |
|---|---|---|---|
| 3,106,021 | 10/1963 | Borden | 433/104 |
| 3,129,511 | 4/1964 | Williams | 433/104 |
| 3,256,603 | 6/1966 | White | 433/104 |
| 3,556,669 | 1/1971 | Valaska | 433/104 |
| 3,646,678 | 3/1972 | McAlister | 433/104 |
| 3,757,425 | 9/1973 | Kraft | 433/98 |
| 3,963,391 | 6/1976 | Thorburn et al. | 433/104 |
| 4,486,174 | 12/1984 | Eibofner | 433/104 |
| 4,544,355 | 10/1985 | Eibofner | 433/104 |

Primary Examiner—John J. Wilson
Attorney, Agent, or Firm—Hughes & Multer

[57] ABSTRACT

An apparatus for providing a maintenance treatment to a dental tool, the apparatus comprising a station to which the tool is able to be detachably mounted, an agent supply means (for supplying an agent used in the maintenance treatment), and a purging substance supply means. The station has agent conduit means and purging conduit means which are able to be detachably connected to passageway means of the dental tool. The agent supply means is arranged to transmit the agent through the agent conduit means in a manner that the agent contacts portions of agent-benefitted portions of the dental tool. The purging substance supply means is arranged to transmit the purging substance through the purging conduit means in a manner that the purging substance is able to remove particles of the agent from portions of agent-detrimented portions of the dental tool.

25 Claims, 10 Drawing Sheets

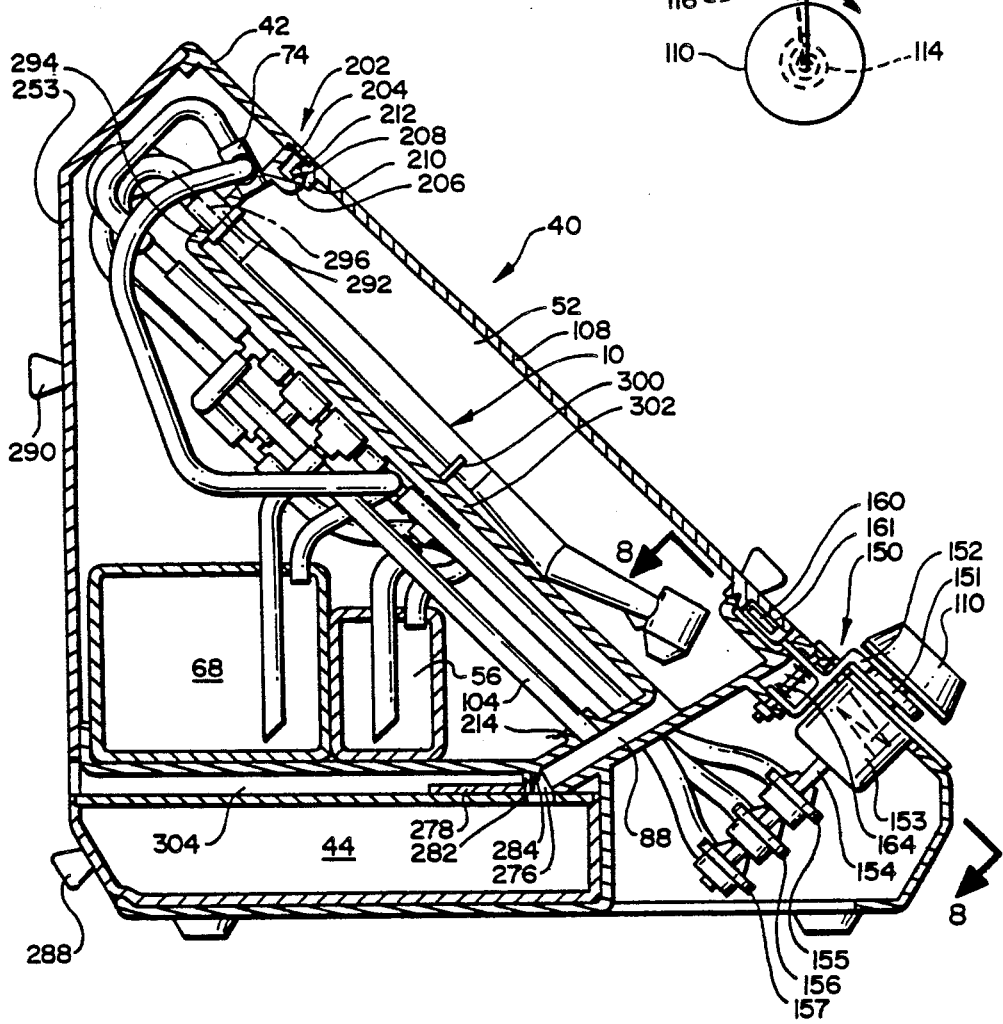

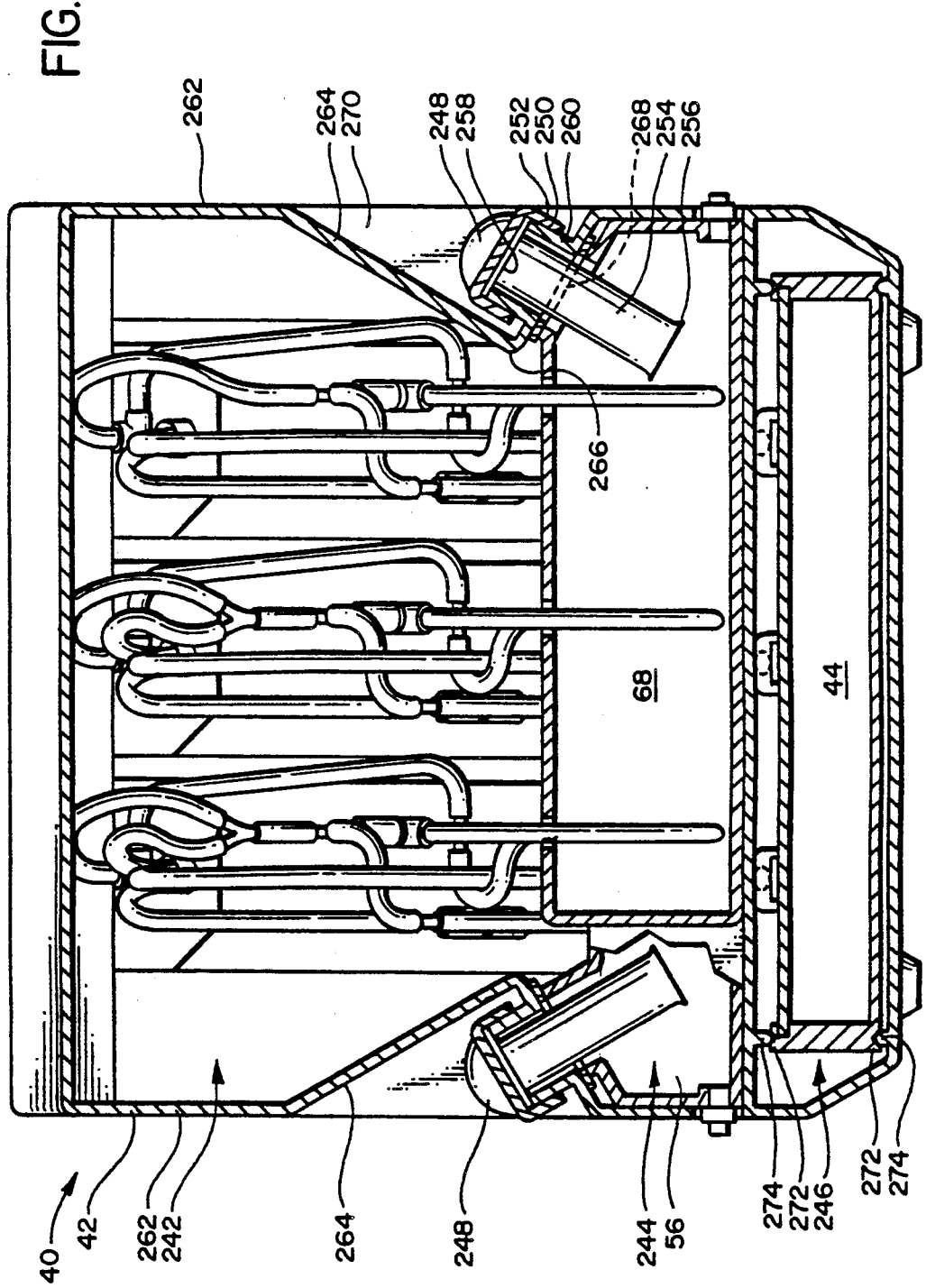

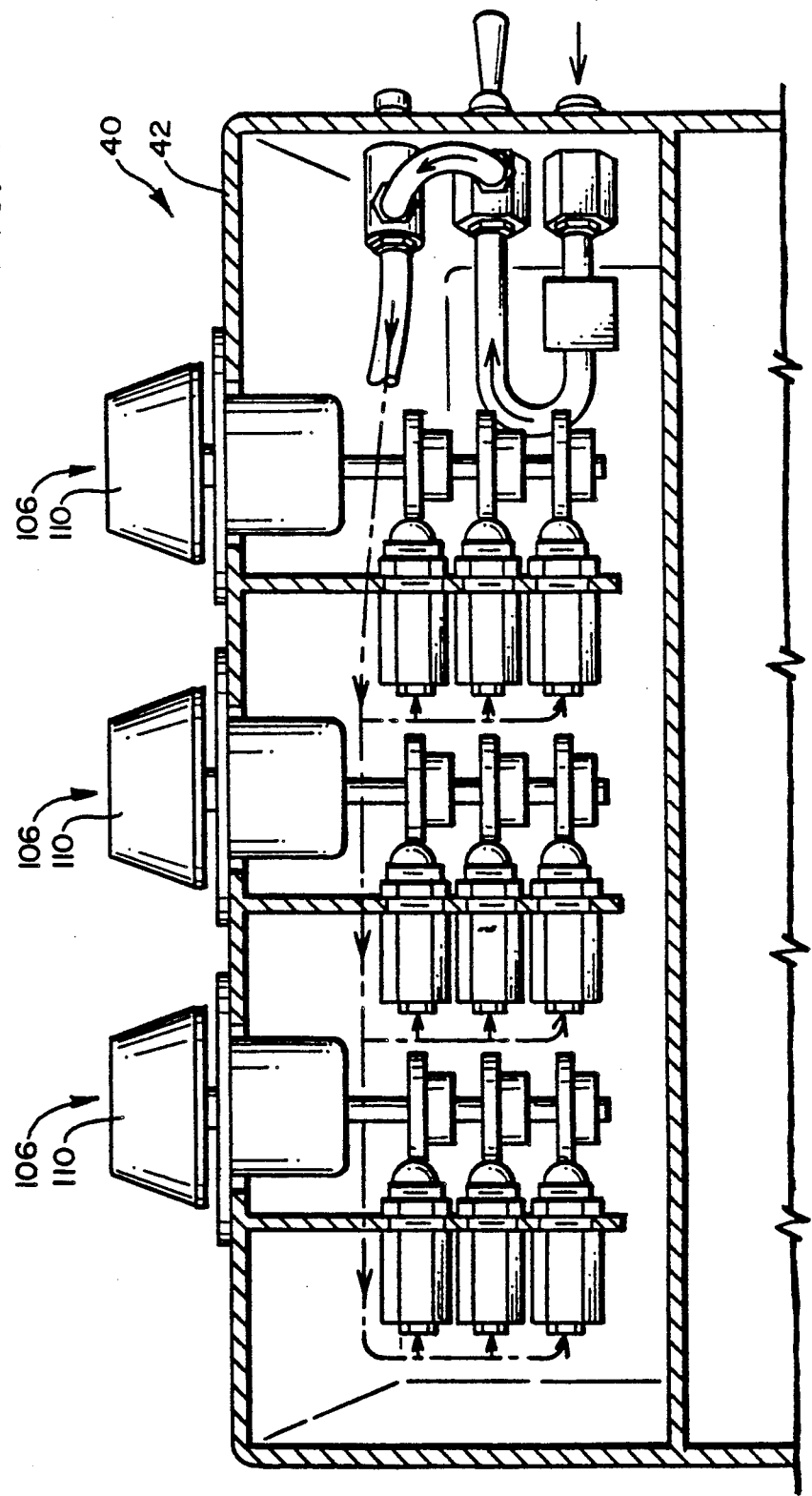

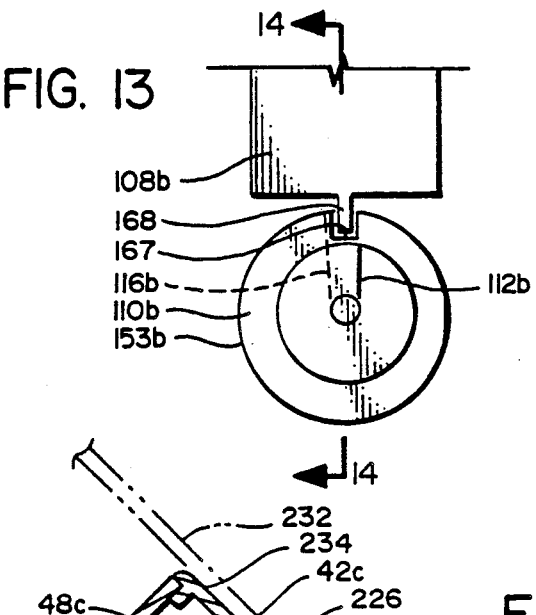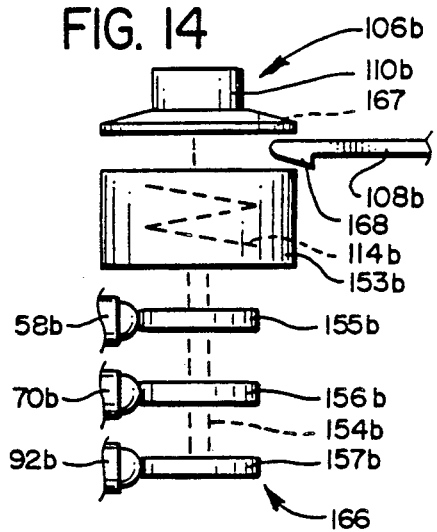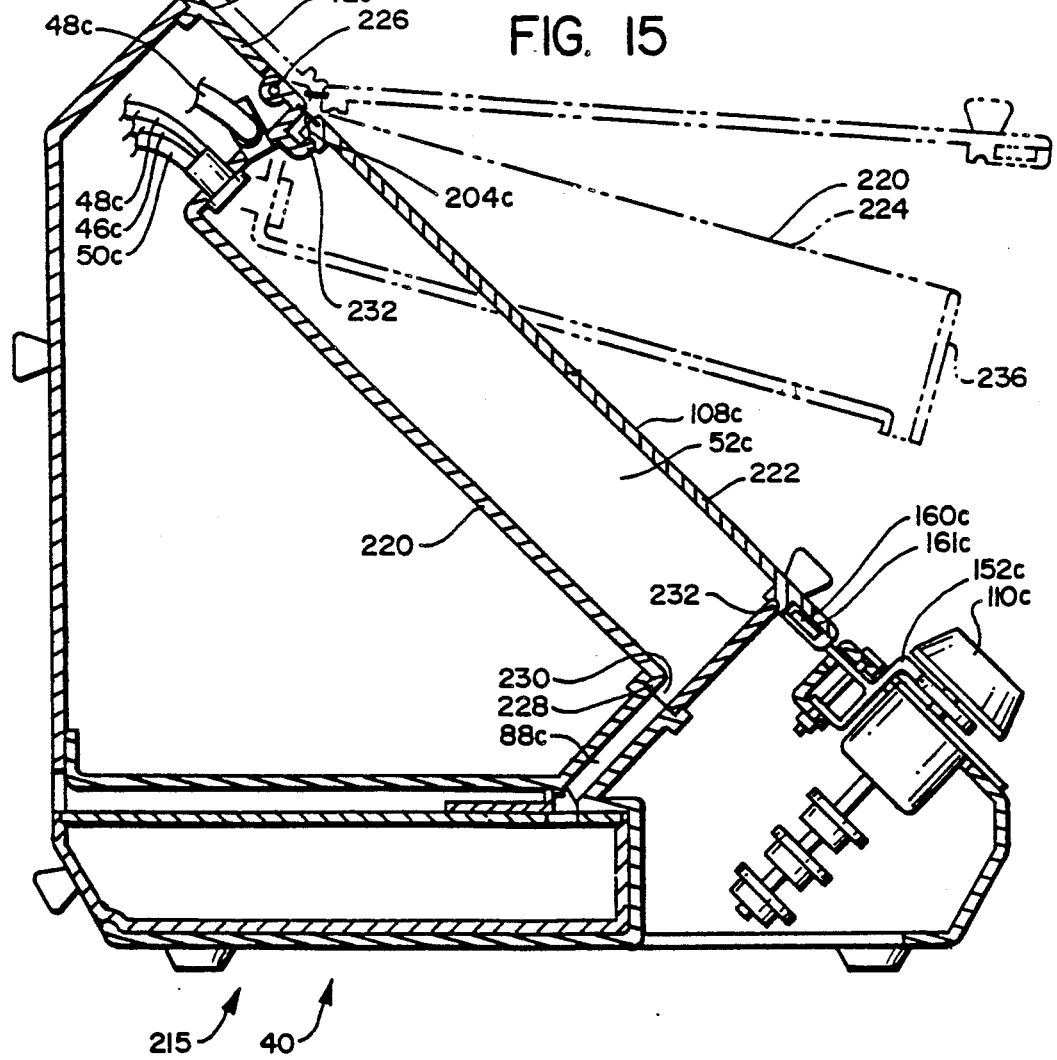

DENTAL TOOL MAINTENANCE APPARATUS AND METHOD

BACKGROUND OF THE INVENTION

1. Technical Field

The present invention relates generally to a method and apparatus which maintains a dental drill or other dental tool, and more particularly to a unit that provides a maintenance treatment to the dental tool.

2. Background art

Hand held dental tools, such as high speed and low speed dental drill or handpieces, are in wide use, and a dentist will commonly use the same dental tool especially the drills for performing several dental operations on different patients in a short period of time. There is a need for a convenient and effective method to help the dentist and his or her staff to maintain and sanitize the tools between operations on patients. Furthermore, a routine is needed that would help to insure that all portions of a handpiece which may have been exposed to one patient's mouth are disinfected prior to use with other patients. Such additional procedure would provide one more safeguard against the spread of disease.

A search of the U.S. Patent literature has developed the following patents:

U.S. Pat. No. 3,646,678 (McAlister) shows a dental drill wherein compressed air from an external source is pumped through the drill, through an air turbine which powers the drill, into a vacuum tube 44 within the drill. In the vacuum tube 44, the air is drawn through a valve v to a vacuum pump. Coolant water, which has been first sprayed on a tooth-drill bit interface within the patient's mouth, is drawn into the drill, through a tube, into the line 44, and through the line 44 to the vacuum pump. In a back flushing mode, the flow in the line 44 is reversed. Medicated liquid flows from a source through the valve v backwardly through the line 44 through the drill and to the tooth-drill bit interface where the medicated liquid is dispensed.

U.S. Pat. No. 3,757,425 (Kraft) shows a system in which, when a selected dental tool among 10, 11, 12, 13, is lifted from a pedestal, its associated spool valve 16, 17, 18, 19, becomes operable. Air bearings in the particular tools 10, 11 are continuously supplied with air during the operation. By depressing a single foot pedal, the dentist causes predetermined liquids to flow to the selected tool. For example, if the dentist picks up the tool 10 and presses the pedal, the tool 10 receives plain water. The tools 11 and 12 also receive water. The tool 13 receives a liquid detergent. The tool 12 and 13, receive lubricating oil for their bearings. Upon the same movement of the pedal all four drills receive air necessary to drive the drill. The liquid lubricating oil runs through a line to a nozzle 170 (shown in FIG. 8) which is located in a middle of a drive air line leading to the air turbine in the drill. The venturi effect of the air passing by the nozzle 170 helps disperse the oil into a fine mist, with the air/oil mixture continuing on into the turbine, where the turbine is lubricated.

U.S. Pat. No. 3,556,669 (Valeska) shows a system the major thrust of which (as stated in col.2, ln. 70–col. 3 ln. 5) is to provide a control system that supplies air having the proper pressure and oil content for dental instruments of any manufacturer by suitable adjustment to the system. Oil is mixed with air in a lubricator 163 using a venturi principle and having an oil drop adjustment screw. Fine tuning of the air-oil mixture is provided by an adjustable valve 96 which in effect short circuits the lubricator 163 in a manner to lower the pressure differential therein, thereby providing a step down adjustment for oil content. Tools 12 and 14, which are the tools requiring oil, are able to be supplied with either oiled air or dry air. A shutoff valve 171 in the line to the drill 12 shuts off oiled air, so that the drill 12 may be driven on dry air. When a valve 178 is closed and a valve 180 is open, dry air alone is supplied to the drill 14. When the valve 178 is open, and the valve 180 is closed, oiled air is supplied to the drill 14.

U.S. Pat. No. 3,256,603 (White) shows a system that sends lubricated dry air through the drive turbine of a dental drill, and which directs water-misted coolant air which is discharged at the head of the drill (col. 7 lns. 21–26).

U.S. Pat. No. 3,106,021 (Borden) shows a control unit for a dental tool where a lubricant is applied to the stream of air which flows to drive the dental tool. The lubricant is directed upwardly through a gooseneck 116 where the lubricant drips into an area to be mixed in air in an air passageway. The flow of the oil can be controlled by the setting of a needle valve.

U.S. Pat. No. 4,544,355 and also U.S. Pat. No. 4,486,174 both issued to Eibofner show a container 1 that contains a liquid maintenance medium (which is a cleaning medium or lubricating medium) and a drive medium, such as compressed air or freon. The maintenance medium is forced through a nozzle where the maintenance medium enters the dental tool.

SUMMARY OF THE INVENTION

An apparatus provides a maintenance treatment to a dental tool. As attributes of the dental tool, the tool is controlled by a dental tool control system, and has agent-benefitted portions, contact with which by an agent used in the maintenance treatment is beneficial, and agent-detrimented portions, prolonged contact with which by excess amounts of the agent is undesirable. The tool has passageway means that are able to communicate with the agent-benefitted portions and the agent-detrimented portions. The apparatus comprises: 1) A station to which the tool is able to be detachably mounted, the station having agent conduit means and purging conduit means which are able to be detachably connected to the passageway means of the tool; 2) an agent supply means that is arranged to supply the agent through the agent conduit means; 3) a purging substance supply means that is arranged to transmit a purging substance through the purging conduit means. The agent is transmitted through the agent conduit means in a manner that the agent will contact portions of the agent-benefitted portions of the tool. The purging substance is transmitted through the purging conduit means in a manner that the purging substance is able to remove particles of the agent from portions of the agent-detrimented portions of the tool. The apparatus is characterized in that it is independent of the dental tool control system.

In a preferred embodiment of the invention, the apparatus further comprises an agent valve means, which directs the agent through the agent conduit means, a purging valve means, which directs the purging substance through the purging conduit means, and a control means. The control means controls the agent valve means and the purging valve means in a manner to selectively cause the agent and the purging substance to flow through the agent and purging conduit means for predetermined lengths of time.

In the preferred embodiment, the control means is operated by power imparted manually. Preferably the control means comprises: Agent cam means, which controls the agent valve means; and, purging cam means, which controls the purging valve means. The agent cam means and the purging cam means both are connected to shaft means, which is rotated so as to selectively activate the agent valve means and the purging valve means by energy from spring means which stores energy manually imparted.

In the preferred embodiment, the agent comprises a disinfectant and a lubricant, and the control means acts in the following sequence: To cause the lubricant to flow through lubricant conduit means into a drive air passageway in the tool and to cause disinfectant to flow through disinfectant conduit means into a coolant passageway within the tool; second, to allow the disinfectant to remain undisturbed in the coolant passageway for a predetermined length of time; third, to direct the purging substance through the purging conduit means. The disinfectant flows for a predetermined length of time, which is zero to sixty seconds, and is then undisturbed in the coolant passageway for one to thirty minutes.

In the preferred embodiment the agent is carried to the tool by air. The purging substance comprises air; an air supply means for the purging air also supplies air for carrying the agent. The agent valve means directs air from the air supply means to an air-agent connection means, which in the preferred embodiment comprises an ejector means, that is connected to an agent container means in a manner that the agent is mixed with the air, so that the air carries the agent through the agent conduit means.

In the preferred embodiment, the agent is made to contact exterior portions of the tool. Preferably the disinfectant is dispensed as a mist which contacts the exterior of the tool. In the embodiment, the agent is carried in a first air stream from an air supply, wherein the air supply supplies a second air stream which is mixed again with agent-carrying air. The station comprises a chamber housing having a chamber means into which the tool is able to be inserted for mounting to the station, and being arranged in a manner that when the tool is mounted thereto, the tool is inclined, a forward end of the tool being lower than a rear end thereof. The chamber means has an air pressure release means. In a second arrangement of the chamber housing, the chamber housing is mounted to the apparatus pivotally.

A method for providing the maintenance treatment to the dental tool comprises: Detachably mounting the tool to the station and attaching the agent conduit means and the purging conduit means to the passageway means of the tool; controlling the agent valve means in a manner that the agent is directed through the agent conduit means for the predetermined length of time so that the agent contacts portions of the agent-benefitted portions of the tool; and, controlling the purging valve means in a manner that the purging substance is directed for the predetermined length of time through the purging conduit means, so that the purging substance is able to remove particles of the agent from portions of the agent-detrimented portions, with the method being characterized in that equipment used therein is independent of the dental tool control system.

BRIEF DESCRIPTION OF THE DRAWINGS

FIG. 4 is a front view of one of three timer windup knobs which are used manually to control the apparatus of the invention;

FIGS. 5, 6, and 7, are left, reduced rear, and reduced underneath views, respectively, of an apparatus housing, all with portions removed for illustration purposes;

FIG. 5 illustrates a first arrangement of a tool enclosing chamber and a first arrangement of a chamber locking mechanism;

FIG. 13 is a schematic view showing a timer knob and a chamber access door, in a second arrangement of chamber locking mechanism;

FIG. 14 is a schematic cross section of the view in FIG. 13 taken along the line 14—14;

FIG. 15 is a view like FIG. 5 but showing an alternative arrangement of tool enclosing chamber;

DESCRIPTION OF THE PREFERRED EMBODIMENT

It is believed that a better understanding of the present invention will be obtained by first describing a typical dental tool for which the present invention is adapted to be used. This will be followed by a description of the several steps accomplished by the present invention on the dental tool, after which there will be a detailed description of the components and operation of the present invention.

Figure 1:
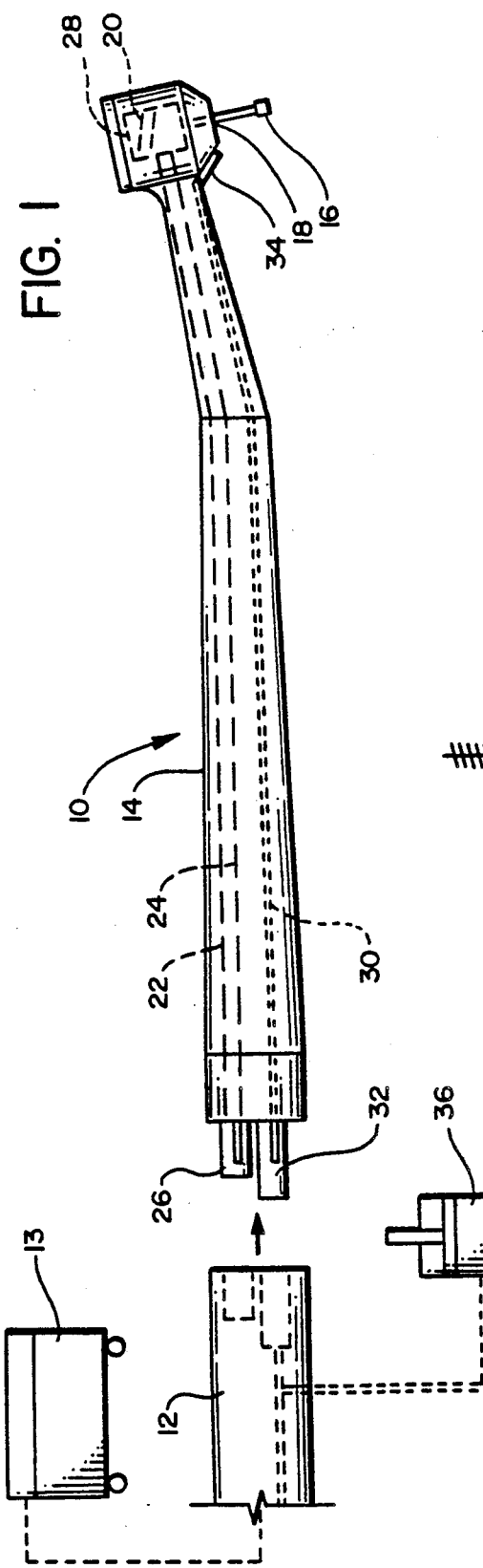
FIG. 1 schematically shows a conventional high speed dental drill with a detachable control hose and a control system for the dental drill.

With reference to FIG. 1, there is shown a typical dental tool which is an air driven high speed drill or handpiece 10 which can be used to perform various dental operations.

This drill 10, which is connected through a detachable control hose 12 to a tool controlling system or dental cart 13, comprises a housing 14 having a forward end and a rear end, with the forward end having operating elements such as a rotating drill element or burr 16 which protrudes through a drill hole 18. More specifically, there is an air turbine 20 to which the drill element is able to be mounted. An air intake passageway 22 leads into the air turbine to cause high speed rotation of the turbine (and consequently high speed rotation of the drill element), with this air being discharged from the air turbine through an air discharge passageway 24 through a discharge opening 26. The air turbine has movable parts including bearings 28 that require lubrication. In the tool there is additionally a water tube 30 which receives water from the hose through a water inlet 32 and which through a spout 34 at the forward end delivers the water to a tooth-drill interface, where the water cools the tooth. Typically this water is carried away by a separate vacuum syringe or the like which a person positions in the patient's mouth during the operation. There is a control pedal (not shown) associated with the dental cart which controls the flow of drive air to the air turbine 20 and water through the water tube 30.

Figure 2:
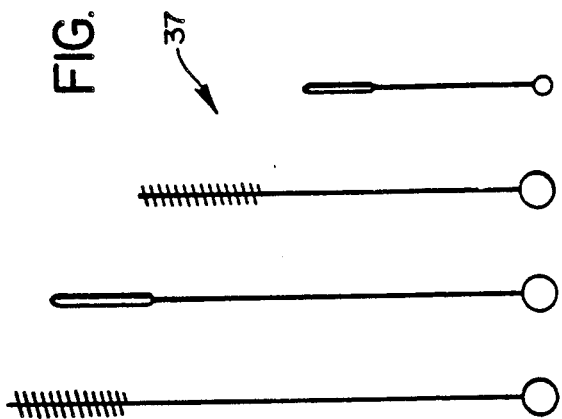
FIG. 2 is a view of conventional brushes used to clean the dental drill of FIG. 1.

When the flow of water is to be stopped, it is desirable to prevent overflow or dribbling. A water retraction means 36 (which is shown schematically) is provided that pulls back the water in the water tube 30 thereby promptly halting the discharge of the water outwardly through the spout 34. Sometimes this backward action pulls fluids from the patient's mouth back through the spout into the water tube 30. If the water tube is not sanitized before the tool is reused on other patients, infection might be spread. Brushes 37 (shown in FIG. 2) are conventionally provided which are used with a disinfectant to clean the water tube.

Figure 3A:
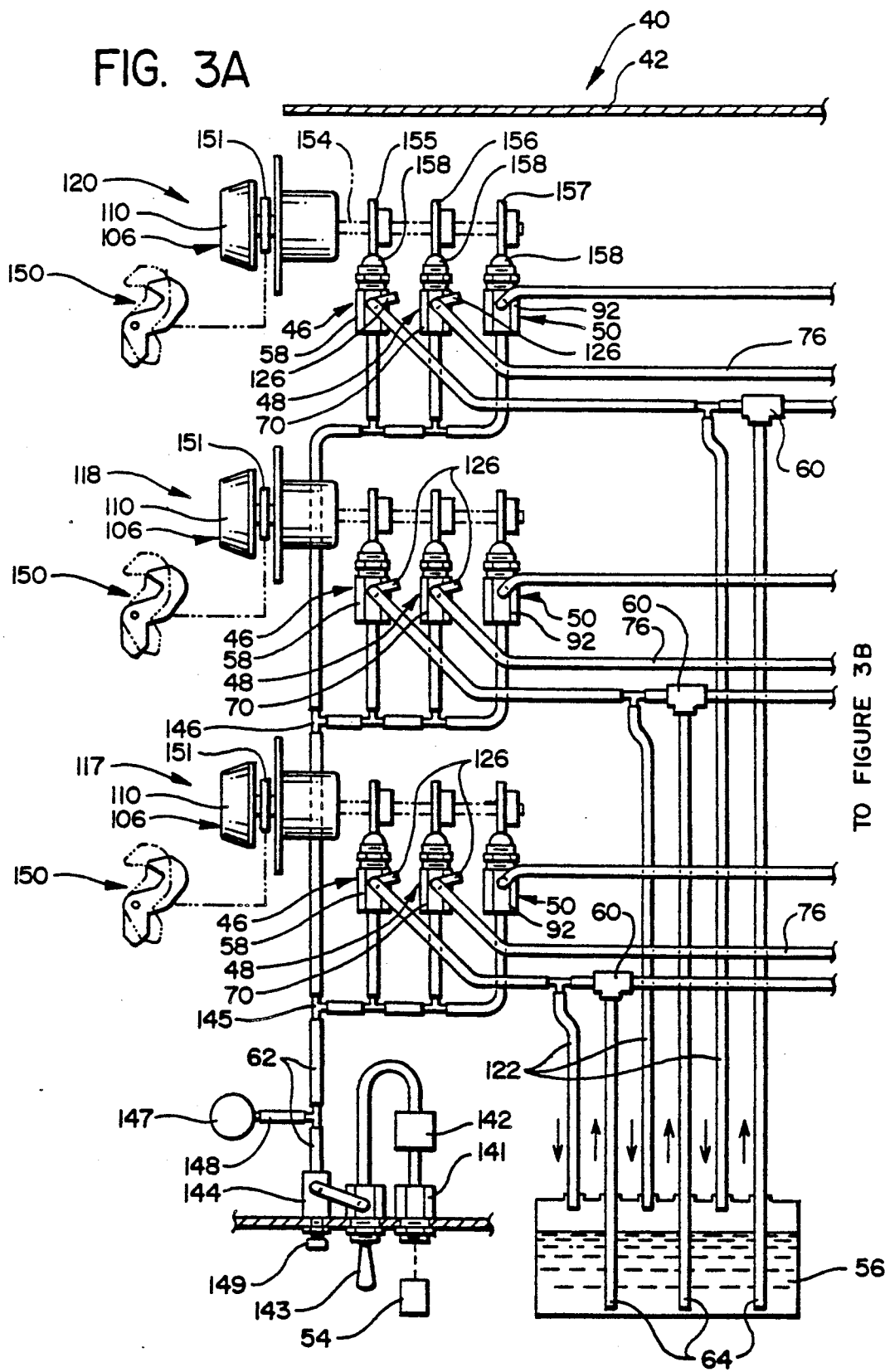
FIGS. 3A and 3B, which appear on two sheets, are schematic flow diagrams of the apparatus of the present invention.
Figure 3B:
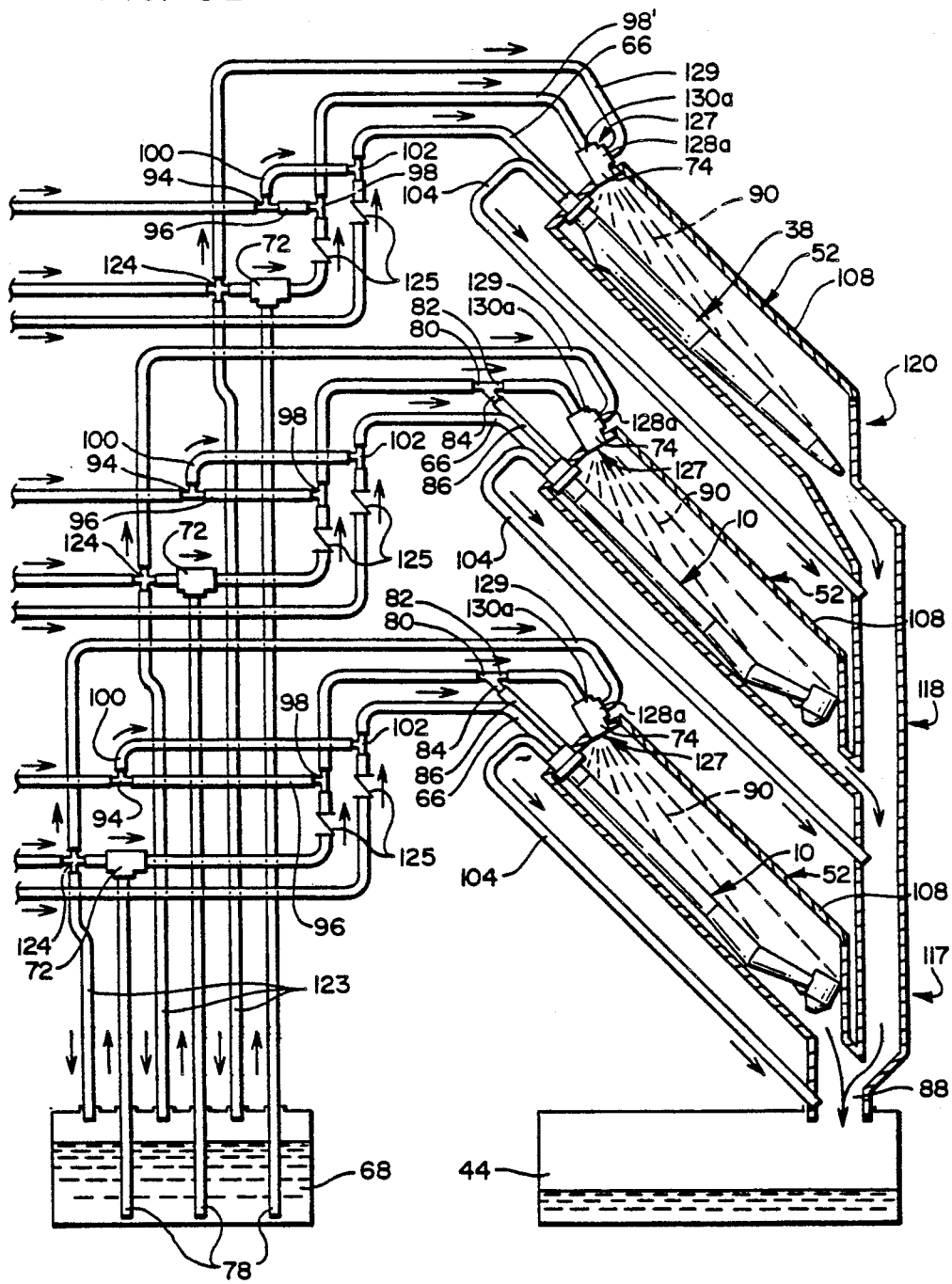

It is to be noted that a low speed/high torque dental drill 38, which is shown at an upper corner of FIG. 3, does not develop the higher temperatures of the high speed drill 10, normally does not require the water coolant, and therefore normally does not use the water tube 30 (even though the drill may be fitted for optional use of the water tube 30).

The apparatus 40 of the present invention shown schematically in FIG. 3 comprises an apparatus housing 42 having three mounting stations to which three separate dental tools, namely two high speed drills 10 and a low speed drill 38 that are not in use are able to be mounted, with the water inlet 32 and the air intake and discharge passageways 22 and 24 of the tools being coupled through couplings to feed pipes, for a maintenance treatment. The apparatus 40 is arranged so that first a stream of air carrying lubricant particles therein passes into the air intake passageway 22 to cause the air turbine 20 and the bearings 28 to rotate and to be evenly lubricated, and then the lubricant carrying air passes through the discharge passageway into a sump 44 (to be described later herein) incorporated in the apparatus 40. The delivery of this lubricant carrying air continues for a relatively short time, as for example two to five seconds, so that the lubricant particles can impregnate the operating components of the air turbine so as to cause a proper application of the lubricant.

Next, a stream of air carrying liquid disinfectant particles therein into the water tube 30 is delivered flushing away any contaminated liquid and killing bacteria and viruses, with the air-sanitizer mixture then to be discharged into the same sump. At the same time, a second portion of the air stream incorporating the disinfectant is sprayed as a mist onto the exterior surface (and into the exposed portions of the hole 18) of the tool to cause disinfecting of those components. The delivery of this disinfectant carrying air continues also for a relatively short time, e.g., two to five seconds.

It is desirable after the application of the lubricant and the sanitizer to have the sanitizing liquid to remain on the components for a length of time, and then to have the residual lubricant and sanitizing material to be removed from the dental tool. A relatively long time, e.g., approximately ten to fifteen minutes, after the application of the lubricant and the disinfectant, pressurized purging air is delivered into the water and air passageways (20, 22, 24, and 30) in the tools with this purging air removing excess particles of the lubricant and the disinfectant. It is to be understood, of course, a sufficient quantity of the lubricant remains in the bearings of the air turbine so as to provide a lubricant coating which is beneficial for the surfaces which move relative to one another in the air turbine. After this is accomplished, the dental tool is able to be removed from the apparatus.

The apparatus of the present invention will now be described in more detail.

In terms of function, the apparatus 40 can be considered as having three main systems. There are a lubricant delivery system 46, a sanitizing system 48, and a purging system 50. As illustrated in FIG. 3, each of these is connected to one of three stations or tool enclosing chambers 52 in which the tool is able to be inserted, detachably mounted, and hooked up for the maintenance treatment. All three of these systems can be operated from a single compressed air source designated 54.

The lubricant delivery system comprises a lubricant bottle 56, and three lubricating subsystems, each comprising a first air valve 58 and a first ejector 60 which is T shaped. The compressed air moves from the source 54 through an air main 62 through the first air valve 58 into the first ejector 60, where the air mixes with particles of the lubricant that move by suction from the lubricant bottle upwardly through a first suction tube 64 also into the first ejector. The air-lubricant mixture is directed out of the first ejector a distance then through a first feed tube 66, through a coupling, into the air intake passageway 22 to the interior of the tool, where the air-lubricant mixture causes the air turbine 20 and bearings 28 to rotate and to be evenly lubricated as previously described.

The sanitizing system comprises a disinfectant bottle 68 which contains liquid disinfectant or sanitizer, and three sanitizing subsystems, each comprising a second air valve 70 (which is identical to the first air valve), a second ejector 72 (which is substantially identical to the first ejector), and an air booster 74, which is described later in more detail and which is similar in configuration to the first and second ejectors, but, as also described later, functions differently. The compressed air is directed through the air main 62, through the second air valve 70, through a line 76, into the second ejector 72, where the air mixes with the liquid disinfectant which is pulled up from the disinfectant bottle through a second suction tube 78 also into the second ejector, with the air-sanitizer mixture continuing out of the second ejector 72 to a Y branch 80, which is used with the high speed drill 10 but not normally with the low speed drill 38 and which has upper and lower legs 82 and 84. The air-sanitizer mixture divides at the Y-branch and moves through the lower leg 84 through a second feed tube 86 through a coupling into the water tube 30 of the tool where the mixture both flushes out contaminants and disinfects the water tube. The flushed contaminants pass out of the spout 34 through a drain passageway 88 into the sump 44. The air-sanitizer mixture that moves through the upper leg 82 continues through the air booster 74 and is dispersed to substantially fill (as indicated by the dashed lines 90) the tool enclosing chamber 52 with a cloud or mist of finely atomized disinfectant particles that envelopes and coats the exterior surfaces and orifices of the tool. (Differences in the sanitizing system when it is intended for use with the low speed drill 38 as opposed to the high speed drill are explained near the end of this application in a section four.)

The purging system comprises three purging subsystems each comprising a third purge air valve 92. The compressed air from the air main moves through the third purge air valve 92 to where it is directed, on the one hand, into the air passageways (20, 22, 24) of the tool, and on the other hand, into the Y-branch 80 where the air divides, a portion of the air passing through the lower leg 84 into the water tube 30 of the tool, the other portion of the air passing through the upper leg 82 through the air booster 74 and into the tool enclosing chamber 52.

More specifically, the purging air is directed from the purge air valve 92 to a branch 94. One leg 96 of the branch joins at a junction 98 to the sanitizing system, with the result that the purging air continues through the Y-branch 80 of the sanitizing system into the water tube 30 of the tool and also into the tool enclosing chamber 52. A different leg 100 joins at a junction 102 to the lubricant delivery system, with the result that the purging air is directed into the air turbine 20 and the air passageways (22, 24) in the tool.

When the purge air passes through the water tube 30 of the tool the purge air expels therefrom residual disinfectant particles which move out the water tube, through the spout 34, through a lower portion of the tool enclosing chamber 52, through the drain passageway 88 into the sump. The purge air also expels residual lubricant from the air turbine 20, the bearings 28, and the air passageways 22 and 24 in the tool in the manner earlier described, the residual lubricant being expelled through the air discharge passageway of the tool, through a coupling, through a discharge line 104, to the same drain passageway 88 and sump.

In this preferred embodiment, the first, second, and third air valves that direct the compressed air to each of the three subsystems are each in turn controlled by a wind up control mechanism or system 106, with the control mechanism also controlling a locking and unlocking of an access door 108 to the tool enclosing chamber 52, the access door 108 remaining locked during the operation of the three systems and becoming unlocked when the last cycle, i.e., the purging cycle, is complete. The control mechanism is controlled manually by a knob or timer knob 110. Pursuant to the arrangement of the control mechanism, the knob 110 is initially in a first unlocked position (shown in FIG. 4) which is indicated by a solid line 112 and in which the access door to the tool enclosing chamber is unlocked. From here, the knob 110 is able manually to be turned clockwise, winding up a spring 114 while rotating to a second cycle starting position which is indicated by a dashed line 116. Once the knob is released from a person's grip in the second cycle starting position, and as the knob is driven by the spring slowly counterclockwise, the control mechanism actuates the valves in order: First the first air valve 58 which is actuated for the short time so as to direct the air through the lubricant delivery system; second the second air valve 70 which is actuated for the short time so as to direct the air through the sanitizing system; and finally the third purge air valve 92 which directs the air through the purging system. The control mechanism 106 turns each of the first, second, and third air valves on and off for the appropriate durations and at the appropriate times as previously described. After the purging cycle is completed, the control mechanism then unlocks the door to the tool enclosing chamber 52, and the knob 110 returns to the first unlocked position.

To review the operation of the invention, the tool is placed in the initially unlocked tool enclosing chamber 52 and is connected through couplings to its water tube 30, and air intake and air discharge passageways. The access door 108 is then closed so as to render the tool enclosing chamber fully enclosed and the knob 110 is simply turned clockwise as far as it will go, acting to cause the access door to lock. The control mechanism or system 106 will act to cause the lubricant delivery system to direct the air-lubricant mixture through the air intake passageway 22 inside the tool to the air turbine 20 and bearings 28. The lubricant benefits the bearings and movable parts of the air turbine, impregnating them with the lubricant. The control system will then cause the sanitizing system to direct the air-sanitizer mixture into the water tube in the tool and to cause the air booster 74 to spray the mist of atomized disinfectant particles to envelope and coat the tool. Since the tool enclosing chamber is enclosed, an appropriate quantity of the disinfectant will be kept in contact with the exterior of the tool, with the disinfectant being prevented from evaporating into the ambient atmosphere. The disinfectant treatment flushes contaminates out of, and kills viruses and bacteria within, the water tube, while also killing viruses and bacteria on the exterior surfaces of the tool. After the relatively long period, e.g., the ten or fifteen minutes, during which the disinfectant will have sufficient time to act thoroughly, the control system will cause the purging system to pump the purge air through the air passageways in the tool to remove excess lubricant, and through the water tube and through the tool enclosing chamber to remove the residual disinfectant from the water tube and from the exterior of the tool. After the end of the purging cycle, the access door will then unlock and the timer knob 110 will return to its original position.

The excess lubricant, if not removed from the interior of the tool, over time is able in many cases to detriment the control hose 12. In particular, the excess lubricant may make brittle an interior lining of the control hose. Additionally, it is helpful to purge the excess disinfectant from the exterior surface of the tool and also from the interior of the water tube, so that the exterior surface is not slippery, and so that a portion of the excess disinfectant does not possibly go into a subsequent patient's mouth.

As previously mentioned there are three tools (38, 10, 10) which independently are serviced by the apparatus as illustrated, therefore there are three copies of the tool station or chamber 52 and the associated drain passageway 88, with three associated copies of each of the operating systems, i.e., the lubricating, sanitizing, purging, and controlling subsystems. Accordingly, the illustrations are organized into three copies or subsystems of all the operating systems, namely a righthand copy or subsystem, which is generally designated 117 and which appears lowermost in FIG. 3 (called "righthand" because it is associated with one of the tool enclosing chambers 52 that is on a righthand side of the actual apparatus housing, i.e., on a righthand side seen in FIG. 17), a middle copy or subsystem which is designated 118, and a lefthand copy or subsystem, which is designated 120 and which appears uppermost in FIG. 3. The righthand and middle copies 117 and 118 are each intended for use with the high speed drill 10 and are identical. The lefthand copy 120 is to be used with the low speed drill 38, and has the differences in the sanitizing system that will be described.

Having described certain major features of the invention, further technical details will now be provided. These will involve:

1. The delivery systems;
2. the ejectors, the air booster, and the main air source;
3. the control mechanism;
4. the differences in the lefthand sanitizing subsystem, which is used with the low speed drill;
5. the positioning of the tool chamber;
6. the access to the tool chamber;
7. the compartment layout.

1. Delivery System Details

In the paragraphs that follow of this section are discussed further details in the delivery systems, i.e., the lubrication delivery system, the sanitizing system, and the purging system as seen in FIG. 3

In addition to the lubricating and sanitizing systems pulling the liquid lubricant and disinfectant from their respective bottles 56 and 68 upwardly through the first and second suction tubes 64 and 78, pressure tubes are provided that pressurize each of the bottles so as to help force the respective liquids up the first and second suction tubes. In particular for each subsystem, there is a first pressure tube 122 which is connected between the first air valve 58 and the lubricant bottle 56; there is also a second pressure tube 123 which is connected at a joint 124 between the second air valve 70 and the disinfectant bottle. In an alternative arrangement, which is not shown, the first pressure tube is not used while the second pressure tube is provided, whereby only the disinfectant bottle receives the additional pressurization. This arrangement permits the lubricant bottle to be of a lighter construction, since it does not have to withstand the higher pressure, however, the advantage of the additional pressure provided by the first pressure tube is given up. Preferably the bottles 56 and 68 when intended to be pressurized as in FIG. 3 have a rounded shape, so as to withstand the pressure.

To prevent during the purging cycle a back flow of the purging air from the junctions 98 and 102 into the second ejector 72 and into the first ejector 60, respectively, check valves 125 are provided in the lines.

To enable the flow of the respective fluids introduced to the tool to be shut off quickly at the ends of the lubricating and sanitizing cycles, the first and second air valves 58, and 70 are arranged so that they are able to connect the lubrication delivery and sanitizing systems, respectively, to either compressed air, through the air main 62, or to the atmosphere, through identical atmosphere ports 126. Thus when these valves 58 and 70 are in an "on" position, the compressed air flows from the air main 62 through the valve, to the lubrication delivery and sanitizing systems, respectively, and when these valves are in an "off" position, the valves connect the lubrication delivery and sanitizing systems, respectively, to the atmosphere. Additionally, this feature depressurizes the lubricating bottle 56 and the sanitizing bottle 68 when the lubricating and sanitizing systems are not in use.

2. The Ejectors, the Air Booster, and the Main Air Source

The first and second ejectors 60, 72 (collectively called herein the "ejectors") and the air booster 74 are very similar in configuration, however, they differ in certain aspects of function. As previously described, the first ejector 60 and the second ejector 72 are used in the lubricating and sanitizing systems, respectively, in which they act to cause the liquid lubricant and liquid disinfectant, respectively, to be pulled up from the bottles and to be mixed with the air stream so as to atomize the liquid and to produce the air-lubricant mixture and the air-disinfectant mixture, respectively. The air booster 74 is used in the sanitizing system like a nozzle to spray within the tool enclosing chamber 52 an air-sanitizer mist which has been augmented with air. As shown in FIG. 3, the air booster 74 is connected to a dispensing end 127 of the sanitizing system. The air booster 74 connects at a side inlet 128a thereof through a line 129, through the joint 124, through the line 76, through the second air valve 70, to the air source 54. (The suffix "a" is used, added to numerical designations herein to denote components of the air booster 74 that in configuration at least, but not necessarily in function, are similar to components of the ejectors having the same numbers). A main inlet 130a of the air booster 74 receives the air-sanitizer mixture from the sanitizing system. The air-sanitizer mixture from the sanitizing system coming in through the main inlet 130a is mixed in the air booster 74 with the dry air coming in through the side inlet 128a, in a manner that the mixture is augmented with air as it is dispersed into the chamber 52.

In terms of function then, the air booster augments the already mixed air-sanitizer mixture with air, and the additional air is able to provide more energy to boost the velocity of the dispensing of the mist. Additionally, it is with some turbulence that the air booster mixes the air-sanitizer mixture and the air, thereby helping to produce the fine mist.

The ejectors 60 and 72 essentially provide first stage atomizing of the respective liquids.

Figure 16:
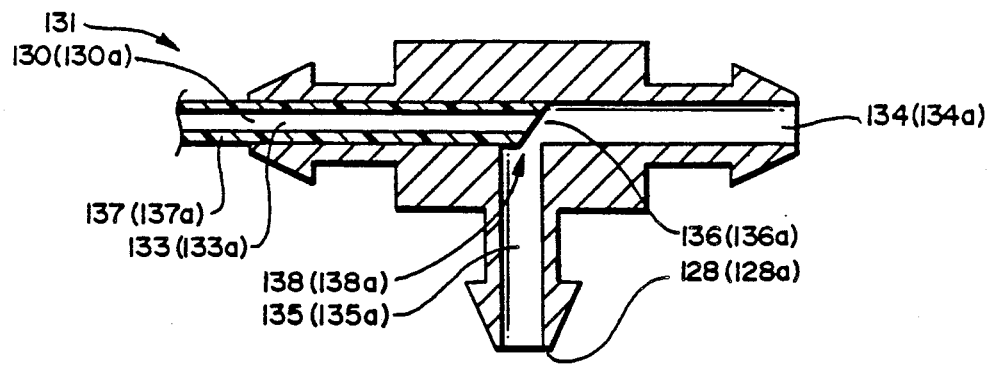
FIG. 16 is a cross section of a component used in the delivery systems of the invention.

As mentioned, the configuration of the ejectors and of the air booster are very similar. As shown in the cross section of FIG. 16, the ejectors and air boosters each have a basic configuration of a typical T-fixture 131 formed as T-shaped housing 132 (132a) comprising: a horizontal main cylindrical bore 133 (133a) with the main inlet 130 (130a) and an outlet 134 (134a); and, a vertical bore 135 (135a) which has the side entrance 128 (128a) and which joins at a junction location 136 (136a) to a middle portion of the horizontal bore 133. The T fixture 131 receives a first fluid (in the cases of the ejectors, the compressed air; in the case of the air booster, the air-sanitizer mixture) which moves, starting at the main inlet 130 (130a), through a first half portion of the horizontal bore through the junction location, into a second half portion of the horizontal bore. A second fluid (in the first ejector, the lubricant; in the second ejector, the disinfectant liquid; and in the air booster, the compressed air) moves from the side inlet 128 (128a) upwardly through the vertical bore, so that the second fluid joins the first fluid at the junction location 136 (136a), becomes mixed in the first fluid, and moves rightwardly through the second half portion of the horizontal bore through the outlet 134 (134a) where the mixture of the fluids leaves the T-fixture.

The T-fixture is illustrated as also having mounted therein in the left half portion of the horizontal bore an inner tube 137 (137a) which begins at the main inlet 130 (130a) and runs to the junction location 136 (136a) where the inner tube ends in a diagonal cut. The inner tube extends across the top ends of the vertical bore for a substantial portion of the diameter of the vertical bore, so that between the diagonally cut end of the inner tube and a right lower portion of the T-fixture's housing in the figure, there is a narrow part 138 (138a), through which the first fluid must pass in order to pass from the vertical bore, into the junction location, into the second half portion of the horizontal bore.

Figure 9:
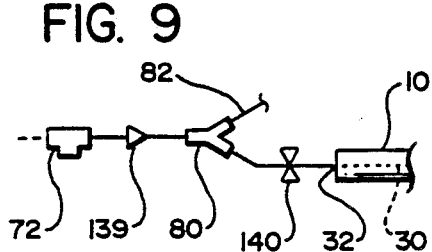
FIG. 9 is a schematic detail of a portion of a sanitizing system of the invention.

To control a rate at which the lubricant and the sanitizer are to be consumed, the first and second suction tubes 64 and 78, should be of a relatively small diameter as for example 1/16th inch (if used with the first and second ejectors having bores 133 and 135 of an 8th inch diameter). This will help to reduce the rate of flow of the lubricant and the disinfectant. Also, as shown in the detail of the sanitizing system of FIG. 9 a reducer 139, such as for example one that reduces a width of the pipe from ⅛ inch to 1/16th inch, is desirably connected between the second ejector 72 and the Y-branch 80 in the sanitizer system. A restrictor 140 which pinches the pipe is desirably placed between the Y-branch and where the air-sanitizer mixture enters the tool 10.

Figure 18:
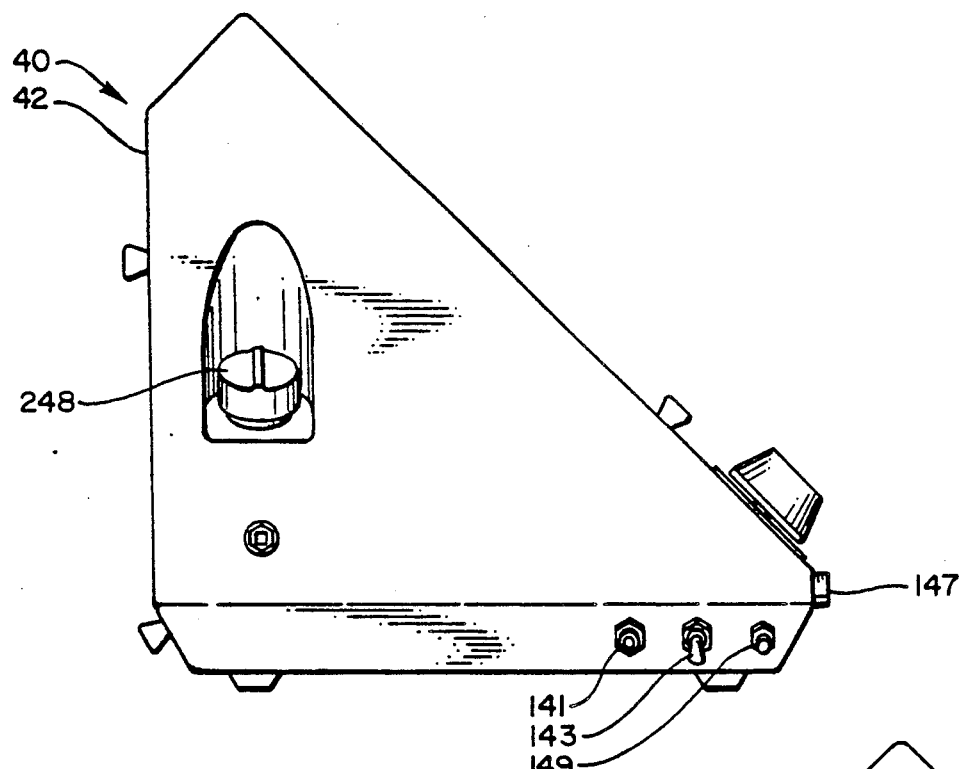
Figure 19:
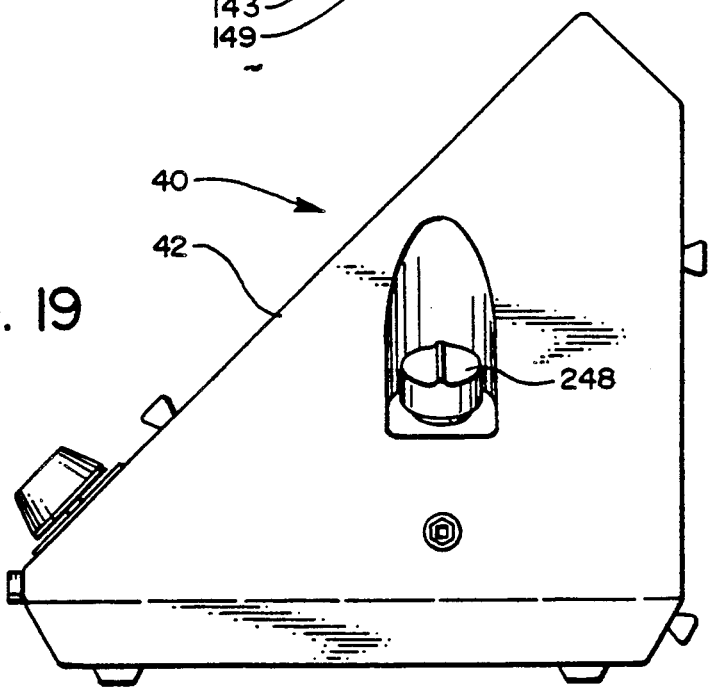

Turning to the main air source as shown in FIG. 3, the compressed air having a high pressure (such as for example 60 PSI) is supplied from the compressed air source 54, which is external to the apparatus. The air then passes through a quick disconnect fixture 141 through an air filter 142, through an on/off switch 143, through a manually operable pressure regulator 144, which through a manually operable pressure regulator 144, which reduces the air pressure to a reduced level (such as for example 20 PSI), and into the air main 62, which leads to right and middle branches 145 and 146, that connect to the right and middle iterations 117 and 118, respectively, of the delivery systems, with the air then continuing through the air main into the left iteration 120 of the delivery systems. A pressure indicator 147 which is connected through a tap 148 between the pressure regulator and the left branch is mounted on the exterior of the apparatus housing (as shown in FIG. 18) as is a pressure regulator knob 149 that controls the pressure regulator. The pressure indicator and the pressure regulator knob are positioned where they may be readily viewed and gripped by the person using the apparatus. A rate of consumption of the liquid lubricant and liquid sanitizer during delivery is desirably about 1 cc per second.

3. The Control Mechanism.

As described earlier, the control mechanism 106 which is manually initiated by turning at least one of each of the three knobs 110 clockwise as far as the knob will go, actuates the related lubricating delivery, sanitizing, and purging subsystems in sequence and at the appropriate times, eventually unlocking the tool enclosing chamber 52 and returning the knob to the first unlocked position. Preferably, the control mechanism is powered just by the windup power imparted by the act of manually winding up the knob 110.

In a first arrangement 150 of locking mechanism which is shown specially in FIG. 5 (and also in FIGS 3 and 8) the main components are the timer knob 110, a door latch cam 151, a specially shaped door latch member 152, a timer drive 153 which drives the control components rotatably, and a cam shaft 154 having three cams, namely, a lubricating, a sanitizing, and purging control cams 155, 156 and 157. As shown in FIG. 3, the lubricating cam, the sanitizing cam, and the purging cam, each operatively engage a related ball shaped follower 158, which is integral with, and actuates, the first lubricating air valve 58, the second sanitizing air valve 70, and the third purge air valve 92, respectively. As indicated in FIG. 10–12, a boss 159 that each of the lubricating, sanitizing, and purging cams 155, 156 and 157 has, is able to be rotated into alignment with an alignment axis x of each of the valves 58, 70, and 92, respectively, and when these bosses are in alignment with the axes x, the valves 58, 70, 92, are each actuated in a manner to direct the compressed air to the lubricating, sanitizing, and purging systems, respectively.

Figure 8:
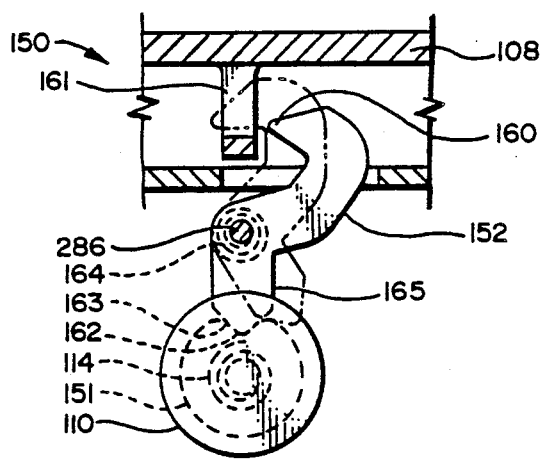
FIG. 8 is a schematic view from the top and front of the first arrangement of the locking mechanism with portions of the apparatus removed for ease of illustration.

As indicated in the front view of the locking mechanism FIG. 8, the knob 110 and the door cam 151 rotate together clockwise and counter clockwise. In the picture, it can be seen that the door latch member 152 has a shape from this viewpoint somewhat like a top of a question mark. The door latch member has a latch portion 160 which fits into a slot 161 in the access door 108 (indicated by diagonal lines) of the tool enclosing chamber 52, in a manner to latch the access door 108 shut. The door cam 151 has a notch 162 shaped like V, while the door latch 152 has a follower end 163 that fits in the notch 162. The door latch 152 is biased in open position by a latch spring 164. The timer drive 153 is biased in a counterclockwise direction by the timer spring 114. The lubricating, sanitizing and purging cams 155, 156, and 157, as shown in FIGS. 10–12, are arranged on the cam shaft 154 relative to one another in a manner than each of the cams has a starting position as shown in the Figures. As shown in FIG. 8, the door cam 151, and the door latch member 152 have a first unlocked position which is shown by a solid line 165 in which the latch portion 160 of the door latch member 152 is withdrawn from the slot 161 in the access door so that the access door is openable. When the knob 110 and the door latch cam 152 rotate clockwise, the door latch member 152 is moved to a locked position which is shown by a hidden line L in which the latch portion 160 of the door latch member is positioned in the slot 161 to lock the access door. As the knob 110 and the door cam 151 are turned clockwise, a left side in the picture of the follower end 163 rides on a periphery of the door cam 151 in a manner that the door latch member 152 is kept in the locked position. When the knob and the door cam have turned 360° clockwise from the first unlocked position, in which the notch 162 is positioned at twelve o'clock in the figure, to a second operating position, in which the notch is also positioned at twelve o'clock, the door cam 151 and the follower end 163 are configured in a manner to ensure that in the second position the door latch member remains in the locked position. As shown in FIG. 5, the knob 110 and door cam 151 are connected operatively to the front of the timer drive 153 in a manner that when a person turns the knob and door cam clockwise, this action will wind up the timer spring 114. When the knob and door cam are released in the second operating position (referring now to FIG. 8), the timer drive turns the knob and door cam counterclockwise. The knob and door cam will continue turning counterclockwise, but will not turn counterclockwise beyond the first unlocked position. Preferably, the timer spring 114 is pre-loaded when the knob and door cam are in the first unlocked position, so that in all the operating positions of the control mechanism, the timer spring is able to exert for the operation of the control mechanism a torque which is sufficient to enable the cams 155, 156, and 157, properly to activate the air valves 58, 70, and 92. The cam shaft 154 and the lubricating, sanitizing, and purging cams 58, 70, and 92 as shown in FIG. 3, are connected to the rear side of the timer drive 153. A ratchet (not shown) within the control mechanism 106 assures that the cam shaft and the lubricating, sanitizing, and purging cams are able to rotate only counterclockwise.

When, after the clockwise-windup of the knob 110 and door cam 151, the knob and door cam are released at their second operating position, the knob, the door cam, the cam shaft 154, and the lubricating, sanitizing and purging cams all rotate together, preferably at a constant speed, until the knob and door cam reach the first unlocked position where the rotation of all of these elements stops.

Figure 10:
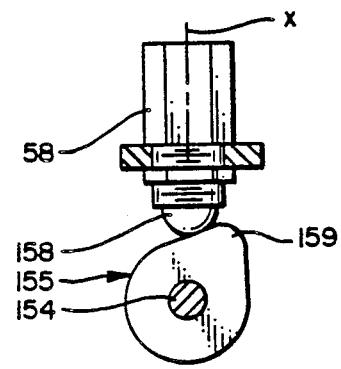
FIGS. 10, 11, and 12, are views of a first lubricating, a second sanitizing, and a third purging air valves, respectively, and associated control cams, all in a cycle starting position.
Figure 11:
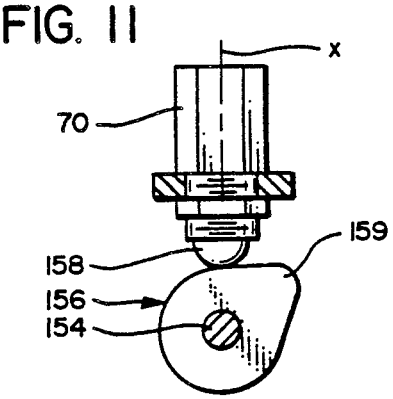
Figure 12:
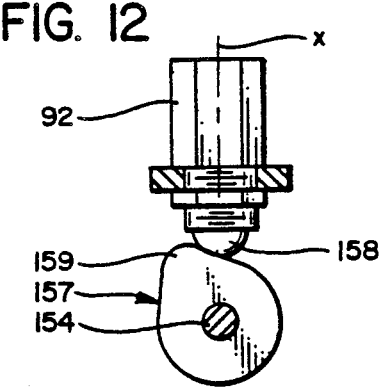

The starting positions shown in FIG. 10-12 of the lubricating, sanitizing, and purging cams are displaced appropriately relative to one another in a manner to provide the previously described desired timing for actuating the first, second, and third air valves, respectively. As shown in FIG. 10, the starting position of the lubricating cam 155 is such that the lubricating cam will actuate the first air valve 58 very shortly after the knob 110 and door cam 151 are released in their second operating position. As shown in FIG. 11, the starting position of the sanitizing cam 156 is such that the sanitizing cam will actuate the second air valve 70 shortly after the actuation of the first air valve. As shown in FIG. 12, the starting position of the purging cam 157 is such that the purging cam will actuate the third air valve 92 only after the relatively long (e.g. 10 or 15 minutes) time during which the disinfectant is allowed to disinfect the exterior and interior portions of the dental tool. Additionally, it can be seen that the starting position of the purging cam is such that shortly after the purging cam has actuated the third air valve the purging cam will be found again in the starting position. The angular positions of starting and of ending for all the cams (the door cam 151, and the lubricating, sanitizing, and purging cams 155, 156, and 157) are preferably identical. The cam shaft 154 and the lubricating, sanitizing, and purging cams, during repeated use of the control mechanism will be rotated clockwise repeatedly through the starting positions of in FIGS. 10-12.

With the first arrangement of the locking mechanism, the operation of the control mechanism 106 is as follows. The knob 110 and the door cam 151 begin in their first unlocked position, while the lubricating, sanitizing, and purging cams begin in their starting positions. After the dental tool is inserted in the tool enclosing chamber 52, and after the access door 108 is closed, the knob is turned with the door cam a full 360° to their second operating position, where the access door will still be locked, and in this position the knob will be released for the person's grip. The knob and door cam, and simultaneously, the cam shaft 154 and the lubricating, sanitizing, and purging cams, begin turning clockwise, actuating in the described order and at the described times, the first, second, and third air valves 58, 70, and 92. Just after the purging cycle is completed, the lubricating, sanitizing, and purging cams will have returned to their starting positions. Simultaneously, the knob 110 and the door cam will have returned to their first unlocked position, and rotation of the control mechanism will then stop. All the elements will have then been repositioned for a new cycle, and the access door 108 will be in an unlocked position, so that the person will be able to retrieve the dental tool from the chamber.

Second Arrangement of the Locking Mechanism—In a second arrangement 166 of locking mechanism, in which components that are similar to components of the first arrangement (150) will have the same numerical designations, with the small letter "b" added, and which is shown in FIGS. 13 and 14, the main components are a timer knob 110b which has a notch 167 on its periphery, an access door 108b which has a tab 168 that fits in the notch 167 in a manner that the tab is allowed to move through the notch, a timer drive 153b biased by a timer spring 114b in a counterclockwise (as viewed in FIG. 13) direction, and a cam shaft 154b, to which are fixedly attached a lubricating, a sanitizing, and purging cams 155b, 156b, and 157b, respectively. Unlike the first arrangement, there is no door cam. The knob has a first unlocked position shown, by the solid line 112b in which the tab of the access door is aligned with the notch 167, so that the access door may be opened.

As in the first arrangement 150 of the locking mechanism, the lubricating, sanitizing, and purging cams on the cam shaft, are arranged to actuate first, second, and third air valves, 58b, 70b, and 92b, respectively, and, in the manner of the first arrangement of locking mechanism as shown in FIGS 10-12, the lubricating, sanitizing, and purging cams have configurations and starting and ending positions that are identical to those described already. Again, the cam shaft 154b is connected to the rear of the timer drive 153b, and a ratchet means within the control mechanism 106b assures that the timer drive will only turn the cam shaft counterclockwise. Additionally, the timer knob is connected to the front of the timer drive in the manner that when a person winds up the knob in a clockwise direction, this will wind up the timer spring 114b in the timer drive.

However, unlike the first arrangement when the person winds the knob from the first unlocked position clockwise 360°, the knob will reach a second unlocked position, which is indicated by a dashed line 116b and in which the notch 167 aligns with the tab 168 of the access door 108b, so that the access door is unlocked. The knob will not turn clockwise beyond this second unlocked position.

When, after such clockwise windup by the person, the person releases the knob at the second unlocked position, the knob, the cam shaft, and the lubricating, sanitizing, and purging cams will all rotate together, counterclockwise, with the lubricating, sanitizing, and purging cams actuating the first, second, and third air valves, respectively, until the knob reaches the first unlocked position where it and all the other rotating components stop.

Reviewing the operation of the second arrangement of locking mechanism, the knob will be found in its first unlocked position in which the access door is unlocked, while the lubricating, sanitizing, and purging cams will all be in their starting positions. After the person has inserted the dental tool in the chamber, and has closed the door, the person will turn the knob a full 360° to its second unlocked position where the door will still be unlocked, and the person will release the knob from this position. The knob will begin turning counterclockwise so that the notch 167 will move out of alignment with the tab 168 of the access door, thereby locking the access door. Simultaneously, the cam shaft will rotate counterclockwise and the lubricating, sanitizing, and purging cams will actuate the first, second and third air valves, respectively, for the durations and at the times previously described. Just after the purge cycle is complete, the lubricating, sanitizing, and purging cams will have returned to their starting positions. Simultaneously, the knob will have returned to its first unlocked position, and the rotation of the elements of the control mechanism will stop. (All the elements of the control mechanism will now be repositioned in their starting positions, so that the control mechanism will be able to be reused from this position.) The access door will have now been unlocked, thereby enabling the person to retrieve the dental tool from the chamber.

As previously mentioned, the control system (106, 106b) with both arrangements 150 and 166 is able to be operated and powered entirely by winding. The control system does not rely on a separate power source. It is to be understood that the present invention may be operated without the control system shown, and that any suitable means may be used to control the sequence and the timing of the actuation of the valves, as for example, an electrical control mechanism, or, simply by manual operation of the individual first, second, and third air valves, 58, 70, and 92. It is desirable that the control mechanism avoid actuating the first, second, and third air valves while the knob 110 is being wound up clockwise.

4. Differences in the Lefthand Sanitizing Subsystem, which is used with the Low Speed Drill.

As previously mentioned, the tool which is to be used in the lefthand chamber 52 is illustrated as the low speed drill 38, which normally does not use the internal water tube (30). Consequently, there is normally no need for the Y-branch (80, 82, 84, 86) in the lefthand copy or subsystem 120 of the sanitizing system. Instead, the second ejector 72 of the sanitizing system connects simply through a line 98' to the main inlet 130a of the air booster 74. The low speed drill 38 still will be coupled to the lubrication delivery system so that the air-lubricant mixture will be passed through the air passageways 22 and 24, and air turbine 20 so as to lubricate the bearings 28. As with the high speed drill 10, it is desirable to remove the excess disinfectant from the exterior surfaces and orifices of the tool 38, and to remove the excess lubricant from the air passageways and the air turbine so that the disinfectant does not go into a subsequent patient's mouth and so that the excess lubricant will not later harm the lining of the control hose 12 of the drill. Accordingly, the drill 38 is benefitted by being treated with the purging cycle. Purging air is directed through the internal air passageways, and, via the air booster 74, to the exterior portions, of the tool.

The illustrated configuration, which serves two high speed drills 10 and one low speed dental drill 38 serves the needs of many dental operatories today, which typically have a 2:1 ratio of high speed drills to low speed drills.

Optionally, the lefthand subsystem 120 could be identical to the middle and righthand subsystems 118 and 117. This is desirable if the water tube 30 of the low speed drill 38 is in fact being used with patients.

5. Position of the Chamber.

As shown in the exposed leftside view of the apparatus of FIG. 5, the tool enclosing chambers 52 are inclined obliquely and downwardly in the direction of flow through the tool of the disinfectant. The slope of the incline, as for example 45°, is selected so that gravity aids the forward flow of the sanitizer both through the water tube 30 and from the air booster 74 to the chamber, while the slope is sufficiently gentle to allow the mist, which is dispersed from the air booster to envelope and coat the entire exterior surface of the tool. In particular, the slope should be gentle enough so that the rearward exterior portions of the tool are able to be coated.

6. Access to the Chamber.

Illustrated are two arrangements for providing access so that a person can insert the tool into, and also remove the tool from, the tool enclosing chamber.

Simple Door Arrangement. In a first arrangement 202 of tool enclosing chamber 52 as shown in FIG. 5, the tool enclosing chambers are each fitted with the access door 108 which is hinged at an upper end by a hinge 204. When in a closed position, the door seals the chamber by receiving a tongue 206 of the wall of the chamber in a groove 208 which is defined between inner and outer ridges 210, 212, that run along the periphery of the door. In this first arrangement, the door is locked in the following manner: The operative latch portion 160 of the latch member 152 which is seen in cross section in the locked position is able to be inserted in the slot 161 in the lower end of the door so as to hold the door locked in the locked position. In the unlocked position, the latch member is rotated so that the latch portion is removed from the slot so that the door is unlocked.

As earlier mentioned, the discharge lines 104 which carry the discharged lubricant from the tool join the drain passageways this junction is designated 214.

Tilt Up Chamber with Auxiliary Door—In an alternative arrangement 215 of tool enclosing chamber, in which components that are like components of the first arrangement 202 will have the same numerical designation but with a little letter "c" added and which is shown in FIG. 15, a tool enclosing chamber 52c as before remains fully connected to the lubricating (46c), sanitizing (48c), and purging (50c) systems. Also, the tool enclosing chamber still drains through the drain passageway 88c. Additionally, the tool enclosing chamber still locks and unlocks by means of the positioning of a door latch member 152c, the latch portion of which engages with the slot in an access door 108c.

However unlike in the first arrangement of tool enclosing chamber, the chamber comprises a moveable enclosure 220 which moves from a closed position which is shown by solid lines 222 pivoting upwardly, to an elevated position shown by hidden lines 224, on a main hinge 226 which in turn is stationed on an apparatus housing 42c. In the elevated position, the delivery systems 46c, 48c, and 50c, remained attached to the tool enclosing chamber 52c, but the drain passageway 88c is separable from the tool enclosing chamber at 228. The tool enclosing chamber has a drain opening 230, which in the closed position of the movable enclosure 200 engages the drain passageway, so that there is a drainage flow connection from the tool enclosing chamber into the drain passageway.

The access door 108c is hingedly attached on a door hinge 204c to the movable enclosure 220, so that the access door may be separately opened with respect to the movable enclosure. In a closed position the access door closes against lips 232 of the movable enclosure with a slot 161c of the access door positioned to receive the latch portion 160c of the door latch member 152c for locking.

In operation beginning in the closed, and locked position, where the access door 108c is closed, and the movable enclosure 220 will be held fast in the closed position. The drain opening 230 will be held in engagement with the drain passageway 88 so that a damage flow connection through the drain passageway will be maintained. When the door latch member 152c is displaced so that the access door is unlocked, a person will first raise the access door 108c to a vertical position indicated by a dashed line 232 in which the access door rests at 234 against the apparatus housing 42c. Using the fingers of the person's one hand, the person will then grip a forward wall 236 of the movable enclosure 220 and raise the movable enclosure to a position where the person can conveniently view the location where the dental tool is to be inserted and mounted in the tool enclosing chamber. With the person's other hand, the person will insert and mount the dental tool in the chamber, and will then lower the movable enclosure 220 to the closed position and move the access door from the vertical position to the closed position, where the person now will be able to turn the knob 110c to lock the tool enclosing chamber and to wind up the timer drive to begin the operation of the operating systems.

7. Compartment Layout

Figure 17:
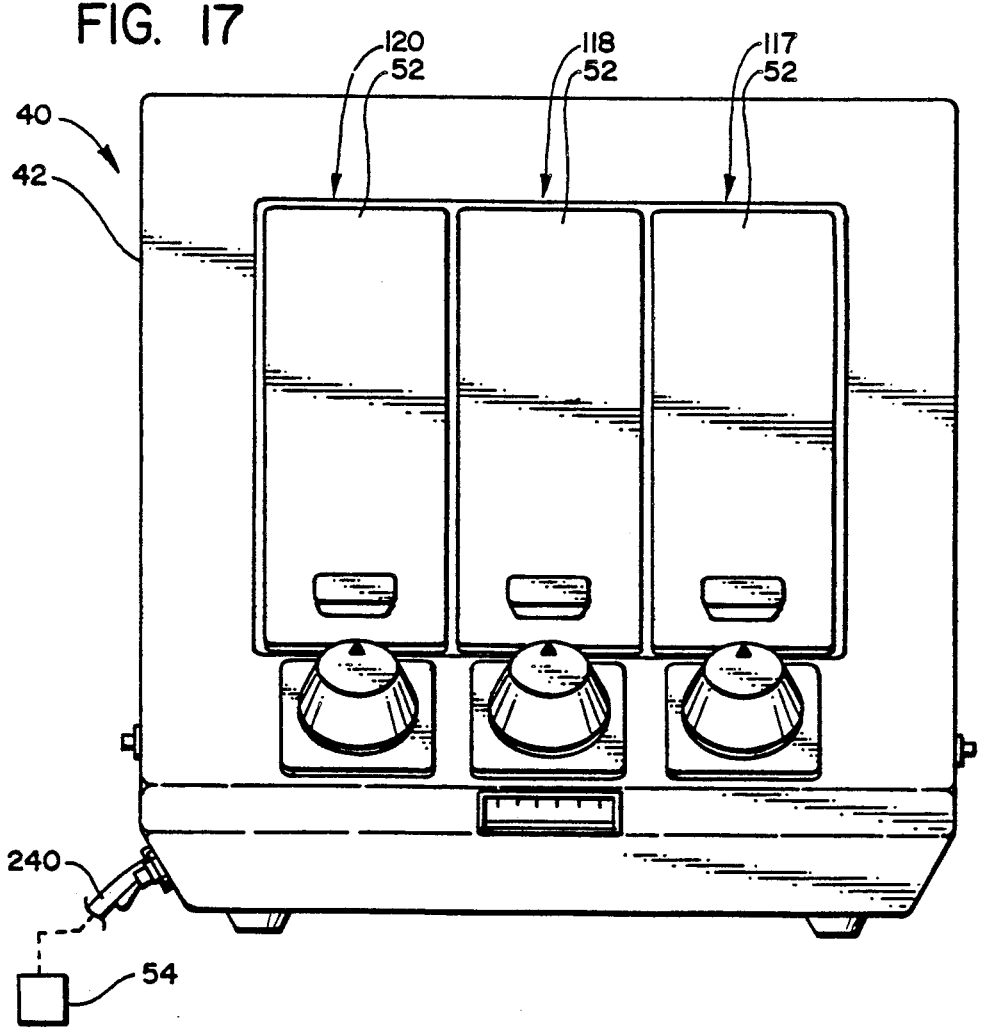
FIGS. 17, 18, and 19 are exterior views of the apparatus housing from the front, the left, and the right, respectively.

As shown in the front exterior view of FIG. 17, the apparatus 40 is housed in the apparatus housing 42 so as to house the apparatus as a compact stand alone unit perhaps 10" in height that may be conveniently positioned on a platform, table, shelf, or the like, and may be easily carried. The compressed air is supplied to the apparatus through a detachable exterior hose 240, which as mentioned detachably connects to the quick disconnect fixture 141. The three tool enclosing chambers 52, which each have an elongated rectangular shape, are arranged side by side.

As seen in the rear exposed view of FIG. 6, the apparatus housing houses three general compartment areas as follows: An upper area 242 which contains the tool enclosing chambers and the tubes and fittings of the operating systems; a middle bottle area 244 which contains the two bottles, the one 56 for the lubricant, and the other 68 for the sanitizer; and a lower sump area 246 in which there is detachably mounted the sump 44, which is formed as an enclosed box, which will be described presently.

In the middle bottle area 244 it is able to be seen that the two bottles 56 and 58 are fixedly mounted in the unit. Each is a rounded container, that fits easily in the available space. As earlier mentioned, one or both of the bottles may be walled of heavier gauge material so as to withstand the pressurization from the pressure tubes 122 and 124 (not shown in FIG. 6, but shown in FIG. 3). Each bottle has a removable twist filler cap 248 which is screwed onto a thread 250 and which has a grip 252. For a person to view the level of the liquid in the bottles, an openable rear door 253 (shown in FIG. 5) to the apparatus housing is opened. When the filler cap 241 is removed from the bottles, a cylindrical movable spout 254 may be pulled up and a circumferential lip 256 on the lower end of the spout may be inserted in a groove 258 in a neck 260 of the bottle, so that the spout is held in place in an upper position and is able easily to be used for pouring liquid into the bottle. To close the bottle, the lip is removed from the groove, the spout is moved downwardly into the bottle and the filler cap is screwed onto the threads. Right and left sidewalls 262 of the apparatus housing each have a downwardly inwardly sloping part 264 which is connected at a right angle turn 266 to a downwardly outwardly sloping portion 268 to form a right angle that defines a bottle tending filler cap alcove 270 which enables the and the spout to be positioned on the apparatus housing at a location where they are easily gripable and fillable, without requiring any protuberance from the unit which may unnecessarily consume table or shelf space.

The sump 44, which as mentioned is configured as a fully enclosed flat box, may be slid into and out of the lower sump area 246 from the rear side of the unit. The sump has grooves 272 which ride on ridges 274 so that the sump is easily slidable into its proper place. This sump unit desirably will have a volume at least equal to the combined volumes of the lubricating and disinfectant bottles.

As seen in FIG. 5, the tool enclosing chambers drain through the drain passageway 88 through an opening 276 into the sump. Thus the sump, whose volume is equal to the sum of the volumes of the bottles, receives both the discharged lubricant and discharged sanitizer. When the sump unit is slid or pulled rearwardly that is, toward the rear of the apparatus housing, an L-shaped sliding door 278 which is shown in an open position in which the opening 276 is open, is moved by action of a suitable resilient means into a closed position, which seals off the opening 276. Thus the sump is fully enclosed and sealed when the person using the sump removes the sump from the apparatus housing. When the sump is slid back into the lower sump area 246, a lip 282 of the L-shaped door is pushed by a ledge 284, which is positioned at an upper side of the bottom of the drain passageway 88 in a manner that the L-shaped door is forced into its open position.

As mentioned there is also the rear door 253; this provides rear access to the interior portions of the apparatus housing.

It is to be noted that the latch member rotates on a pivot 286 as shown in FIG. 8. The sump 44 the rear door 253 each have pull knobs 288 and 290, respectively, as shown in FIG. 5. As also shown in FIG. 5, a feed tube housing 292 is rotatably mounted in an opening in an upper wall 294 of the tool enclosing chamber 52 for rotation about an axis 296, as also shown in FIG. 5. Additionally, a cradle 300 is provided to support the tool 10 and keep the tool separated from a floor 302 of the chamber.

A horizontal gap area 304 is provided which is at atmospheric pressure and which communicates via the drain passageway 88 with the chamber 52. this is necessary to relieve air pressure buildup in the chamber resulting from discharge of the fluids through the air booster 74.

It is to be understood that various modifications of the foregoing description are able to be made without departing from the basic teachings of the invention.

What is claimed is:

1. An apparatus for providing a maintenance treatment to a dental tool that is controlled by a dental tool control system and which has agent-benefitted portions, contact with which by an agent used in said maintenance treatment is beneficial, and agent-detrimented portions, prolonged contact with which by excess amounts of said agent is undesirable, said tool having passageway means that are able to communicate with said agent benefitted portions and said agent detrimented portions, said apparatus comprising:

a. a station to which said tool is able to be detachably mounted, said station having agent conduit means and purging conduit means, said agent conduit means and said purging conduit means being able to be detachably connected to said passageway means of said tool;

b. an agent supply means that is arranged to transmit said agent through said agent conduit means in a manner that said agent contacts portions of said agent-benefitted portions of said tool;

c. a purging substance supply means that is arranged to transmit a purging substance through said purging conduit means in a manner that said purging substance is able to remove particles of said agent from portions of said agent-detrimented portions, said apparatus being characterized in that it is independent of said dental tool control system.

2. The apparatus as recited in claim 1, further comprising:

a. agent valve means which directs said agent through said agent conduit means;

b. purging valve means which directs said purging substance through said purging conduit means;

c. control means which controls said agent valve means and said purging valve means in a manner to selectively cause said agent and said purging substance to flow through said agent and purging conduit means for predetermined lengths of time, said purging substance flowing for a length of time which is sufficient to remove particles of said agent from portions of said agent-detrimented portions of said tool.

3. The apparatus as recited in claim 2, wherein mechanical power is imparted manually to operate said control means.

4. The apparatus as recited in claim 2, wherein said control means comprises:

a. agent cam means which controls said agent valve means;

b. purging cam means which controls said purging valve means, said agent cam means and purging cam means both being connected to shaft means, said shaft means being rotated so as to selectively activate said agent valve means and said purging valve means by energy from spring means which stores energy manually imparted to said spring means.

5. The apparatus as recited in claim 2, wherein said agent comprises a disinfectant and said control means acts in the following sequence: to cause said disinfectant to flow through disinfectant conduit means into a coolant passageway within said tool; second, to allow said disinfectant to remain undisturbed in said coolant passageway for a predetermined length of time; third, to direct said purging substance through said purging conduit means.

6. The apparatus as recited in claim 5, wherein:

a. said agent also comprises a lubricant which flows through a lubricant conduit means into a drive air passageway means in said tool;

b. said disinfectant flows for a predetermined length of time which is zero to 60 seconds;

c. said disinfectant is undisturbed in said coolant passageway in said tool for one to thirty minutes.

7. The apparatus as recited in claim 2, wherein said agent is carried to said tool by air.

8. The apparatus as recited in claim 7, wherein said purging substance comprises air, and said purging substance supply means comprises an air supply means which also supplies air for carrying said agent through said agent conduit means.

9. The apparatus as recited in claim 8, wherein said agent valve means directs air from said air supply means to an air-agent connection means that is connected to an agent container means in a manner that said agent is mixed with said air so that said air carries said agent through said agent conduit means.

10. The apparatus as recited in claim 9, wherein said air-agent connection means comprises an ejector means having main inlet means through which said air enters said ejector means, side inlet means through which said agent enters said ejector means, and outlet means through which agent-carrying air exits from said ejector means.

11. The apparatus as recited in claim 2, said apparatus comprising a plurality of said stations which are independently operable and which are able to serve high speed dental drills and at least one low speed dental drill, wherein said agent conduit means and said purging conduit means are able to connect to said passageways in said tool through a feed tube housing which is mounted rotatably to said station.

12. The apparatus as recited in claim 1, wherein said agent is conducted from said agent conduit means in such a manner that said agent is able to contact exterior portions of said tool.

13. The apparatus as recited in claim 12, wherein said station comprises a chamber housing having a chamber means into which said tool is able to be inserted for mounting to said station.

14. The apparatus as recited in claim 13, wherein said chamber means is arranged so that when said tool is mounted to said station said tool is inclined, a forward end of the tool being lower than a rear end thereof, whereby a rate of descent of said agent is controlled.

15. The apparatus as recited in claim 13 further comprising:

a. agent valve means which directs said agent through said agent conduit means;

b. purging valve means which directs said purging substance through said purging conduit means;

c. a control means which controls said agent valve means and said purging valve means in a manner to selectively cause said agent and said purging substance to flow through said agent conduit means and said purging conduit means for predetermined lengths of time.

16. The apparatus as recited in claim 15, wherein a door means of said chamber locks after said tool is mounted in said chamber, and, after a flow of said purging substance is completed, said control means acts to cause said door means to unlock.

17. The apparatus as recited in claim 16, wherein said control means comprises a wheel means which, for starting said maintenance treatment, is manually wound in a first sense so as to cooperate with a door controlling member to lock said door means, and which, having rotated in a second sense during said maintenance treatment, acts to unlock said door means at an end of said maintenance treatment.

18. The apparatus as recited in claim 12, wherein said agent comprises disinfectant and is carried in an air stream and dispensed as a mist which comes into contact with said exterior portions of said tool.

19. The apparatus as recited in claim 18, said apparatus further comprising an ejector having a main inlet means through which air from said agent valve means enters said ejector, a side inlet means through which said agent enters said ejector, and an outlet means, through which, after combining, said agent-carrying air exits from said ejector.

20. The apparatus as recited in claim 18, wherein said agent is carried in a first air stream from an air supply; wherein said air supply supplies a second air stream which is mixed again with agent-carrying air, whereby an air content of said agent-carrying air is augmented.

21. An apparatus for providing a maintenance treatment to a dental tool which is controlled by a dental tool control system external to the tool, said tool having passageway means, said apparatus comprising:

a. a station to which said tool is able to be detachably mounted, said station having agent conduit means and purging conduit means, said agent conduit means and purging conduit means being able to be detachably connected to said passageway means of said tool;

b. an agent supply means that is arranged to supply said agent through said agent conduit means;

c. a purging substance supply means that is arranged to supply a purging substance through said purging conduit means, wherein said agent is able to be conducted from said agent conduit means in such a manner that said agent is able to contact exterior portions of said tool, said apparatus being characterized in that it is independent of said dental tool control system.

22. The apparatus as recited in claim 21, wherein said station comprises a chamber housing having a chamber means into which said tool is able to be inserted for mounting to said station, said chamber having air pressure relief means.

23. The apparatus as recited on claim 22, wherein said chamber housing is mounted to said apparatus pivotally.

24. The apparatus as recited claim 21, wherein said apparatus is housed in an apparatus container containing less than five cubic feet and comprising an upper, a middle, and a lower areas, said lower area including a removably mounted sump which is able to be removed for emptying from said apparatus container, said middle area including said agent supply means, with said agent supply means having a filling nozzle means which has a collapsed position and an extended position, in which said filling nozzle receives said agent into said agent supply means.

25. A method for providing a maintenance treatment to a dental tool which is controlled by a dental tool control system external to the tool and which has agent-benefitted portions, contact with which by an agent used in said maintenance treatment is beneficial and agent-detrimented portions, prolonged contact with which by excess amounts said agent is undesirable, said tool having passageway means that are able to communicate with said agent-benefitted portions and said agent-detrimented portions, said method comprising:

a. detachably mounting said tool to a station and attaching agent conduit means and purging conduit means to said passageway means of said tool;

b. controlling agent valve means which control a flow of said agent through said agent conduit means in a manner that said agent is directed through said agent conduit means for a predetermined length of time so that said agent contacts portions of said agent-benefitted portions of said tool;

c. controlling purging valve means which controls a flow of said purging substance through said purging conduit means in a manner that said purging substance is directed for a predetermined length of time through said purging conduit means so that said purging substance is able to remove particles of said agent from portions of said agent-detrimented portions, said method being characterized in that equipment used therein is independent of said dental tool control system.

* * * * *